United States Patent
Xu et al.

(10) Patent No.: US 9,545,622 B2
(45) Date of Patent: Jan. 17, 2017

(54) ACTIVATION AND USE OF HYDROALKYLATION CATALYSTS

(75) Inventors: Teng Xu, Houston, TX (US); Edward Andrew Lemon, Jr., Mickleton, NJ (US); Terry Eugene Helton, Bethlehem, PA (US); Tan-Jen Chen, Kingwood, TX (US); Charles Morris Smith, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 57 days.

(21) Appl. No.: 13/821,957

(22) PCT Filed: Sep. 20, 2011

(86) PCT No.: PCT/US2011/052241
§ 371 (c)(1),
(2), (4) Date: Jun. 6, 2013

(87) PCT Pub. No.: WO2012/050751
PCT Pub. Date: Apr. 19, 2012

(65) Prior Publication Data
US 2013/0289323 A1  Oct. 31, 2013

Related U.S. Application Data

(60) Provisional application No. 61/391,845, filed on Oct. 11, 2010.

(30) Foreign Application Priority Data

Dec. 7, 2010 (EP) .................................... 10194026

(51) Int. Cl.

| | | |
|---|---|---|
| *B01J 29/06* | (2006.01) | |
| *B01J 29/74* | (2006.01) | |
| *B01J 29/068* | (2006.01) | |
| *B01J 29/76* | (2006.01) | |
| *B01J 29/072* | (2006.01) | |
| *B01J 29/064* | (2006.01) | |
| *B01J 29/70* | (2006.01) | |
| *B01J 29/72* | (2006.01) | |
| *B01J 37/18* | (2006.01) | |
| *C07C 2/74* | (2006.01) | |
| *B01J 37/08* | (2006.01) | |

(52) U.S. Cl.
CPC ........... *B01J 29/7476* (2013.01); *B01J 29/061* (2013.01); *B01J 29/064* (2013.01); *B01J 29/068* (2013.01); *B01J 29/072* (2013.01); *B01J 29/7088* (2013.01); *B01J 29/7276* (2013.01); *B01J 29/7676* (2013.01); *B01J 37/18* (2013.01); *C07C 2/74* (2013.01); *B01J 37/088* (2013.01); *B01J 2229/20* (2013.01); *B01J 2229/40* (2013.01); *B01J 2229/42* (2013.01); *C07C 2101/14* (2013.01); *C07C 2529/70* (2013.01); *C07C 2529/74* (2013.01); *C07C 2529/76* (2013.01); *Y02P 20/52* (2015.11)

(58) Field of Classification Search
USPC ................ 502/60, 63, 64, 66, 69, 73, 74, 85
See application file for complete search history.

(56) References Cited

U.S. PATENT DOCUMENTS

| | | |
|---|---|---|
| 3,412,165 A | 11/1968 | Slaugh et al. |
| 3,644,565 A | 2/1972 | Biale |
| 3,760,017 A | 9/1973 | Arkell et al. |
| 3,760,018 A | 9/1973 | Suggitt et al. |
| 3,760,019 A | 9/1973 | Crone, Jr. et al. |
| 3,784,617 A | 1/1974 | Suggitt et al. |
| 3,784,618 A | 1/1974 | Suggitt et al. |
| 3,839,477 A | 10/1974 | Suggitt et al. |
| 3,864,421 A | 2/1975 | Suggitt |
| 3,957,687 A | 5/1976 | Arkell et al. |
| 4,021,490 A | 5/1977 | Hudson |
| 4,094,918 A | 6/1978 | Murtha et al. |
| 4,122,125 A | 10/1978 | Murtha et al. |
| 4,152,362 A | 5/1979 | Murtha |
| 4,177,165 A | 12/1979 | Murtha et al. |
| 4,206,082 A | 6/1980 | Murtha et al. |
| 4,219,689 A | 8/1980 | Murtha |
| 4,268,699 A | 5/1981 | Murtha |
| 4,329,531 A | 5/1982 | Murtha et al. |
| 4,439,409 A | 3/1984 | Puppe et al. |
| 4,447,554 A | 5/1984 | Murtha et al. |
| 4,826,667 A | 5/1989 | Zones et al. |
| 4,954,325 A | 9/1990 | Rubin et al. |
| 4,962,250 A | 10/1990 | Dessau et al. |

(Continued)

FOREIGN PATENT DOCUMENTS

| | | |
|---|---|---|
| EP | 0 293 032 | 11/1988 |
| EP | 0 338 734 | 10/1989 |

(Continued)

OTHER PUBLICATIONS

Chilekar et al., "*Bubble Size Estimation in Slurry Bubble Columns from Pressure Fluctuations*", AIChE Journal, 2005, vol. 51, No. 7, pp. 1924-1937.

(Continued)

*Primary Examiner* — Elizabeth Wood
(74) *Attorney, Agent, or Firm* — Stephen A. Baehl

(57) ABSTRACT

A hydroalkylation catalyst comprising a molecular sieve and a compound of a hydrogenation metal is activated by treating the catalyst at a temperature of less than about 250° C. in the presence of hydrogen.

13 Claims, 2 Drawing Sheets

(56) References Cited

U.S. PATENT DOCUMENTS

| | | | |
|---|---|---|---|
| 5,037,538 A | 8/1991 | Chin et al. | |
| 5,053,571 A | 10/1991 | Makkee | |
| 5,108,969 A | 4/1992 | Del Rossi et al. | |
| 5,146,024 A | 9/1992 | Reed | |
| 5,236,575 A | 8/1993 | Bennett et al. | |
| 5,250,277 A | 10/1993 | Kresge et al. | |
| 5,292,976 A | 3/1994 | Dessau et al. | |
| 5,334,795 A | 8/1994 | Chu et al. | |
| 5,362,697 A | 11/1994 | Fung et al. | |
| 5,384,296 A | 1/1995 | Tsao | |
| 5,554,274 A | 9/1996 | Degnan et al. | |
| 5,557,024 A | 9/1996 | Cheng et al. | |
| 5,705,729 A | 1/1998 | Huang | |
| 5,865,986 A * | 2/1999 | Buchanan et al. | 208/65 |
| 6,037,513 A | 3/2000 | Chang et al. | |
| 6,077,498 A | 6/2000 | Diaz Cabanas et al. | |
| 6,133,470 A | 10/2000 | Beck et al. | |
| 6,204,344 B1 | 3/2001 | Kendrick et al. | |
| 6,489,529 B1 | 12/2002 | Cheng et al. | |
| 6,506,953 B1 | 1/2003 | Cheng et al. | |
| 6,730,625 B1 | 5/2004 | Chang et al. | |
| 6,781,025 B2 | 8/2004 | Dandekar et al. | |
| 6,936,744 B1 | 8/2005 | Cheng et al. | |
| 7,847,128 B2 | 12/2010 | Chen et al. | |
| 7,910,778 B2 | 3/2011 | Chen et al. | |
| 7,910,779 B2 | 3/2011 | Chen et al. | |
| 2002/0065445 A1 | 5/2002 | Arrivat et al. | |
| 2004/0092757 A1 | 5/2004 | Oguchi et al. | |
| 2005/0020435 A1* | 1/2005 | Beck et al. | 502/63 |
| 2005/0020784 A1 | 1/2005 | Noll | |
| 2005/0158238 A1 | 7/2005 | Tatsumi et al. | |
| 2007/0003450 A1 | 1/2007 | Burdett et al. | |
| 2008/0027256 A1 | 1/2008 | Roth et al. | |
| 2008/0027259 A1 | 1/2008 | Roth et al. | |
| 2008/0045768 A1 | 2/2008 | Roth et al. | |
| 2008/0064910 A1* | 3/2008 | Boldingh et al. | 585/475 |
| 2008/0183025 A1* | 7/2008 | Van Broekhoven et al. | 585/722 |
| 2009/0286670 A1* | 11/2009 | Clark et al. | 502/64 |

FOREIGN PATENT DOCUMENTS

| | | |
|---|---|---|
| EP | 0 900 590 | 3/1999 |
| EP | 2 123 622 | 11/2009 |
| WO | 95/31421 | 11/1995 |
| WO | 97/17290 | 5/1997 |
| WO | 01/53236 | 7/2001 |
| WO | 01/74767 | 10/2001 |
| WO | 2005/118476 | 12/2005 |
| WO | 2009/038900 | 3/2009 |
| WO | 2009/107927 | 9/2009 |
| WO | 2010/098798 | 9/2010 |

OTHER PUBLICATIONS

I. Borodino et al., "Hydroalkylation of Benzene and Ethylbenzene over Metal Containing Zeolite Catalysts", Microporous and Mesoporous Materials, 2007, vol. 105, pp. 181-188.

W. Fan et al., "Synthesis and Catalytic Properties of a New Titanosilicate Molecular Sieve with the Structure Analogous to MWW-type Lamellar Precursor", Journal of Catalysis, 2006, vol. 243, pp. 183-191.

S. Kim et al., "Structural Evolution of B-MCM-36 and B-ITQ-2 from B-MCM-22", Bull. Korean Chem. Society, 2006, vol. 27, No. 10, pp. 1693-1696.

S. Lawton et al., "Zeolite MCM-49: A Three-Dimensional MCM-22 Analogue Synthesized by in Situ Crystallization", Journal of Physical Chemistry, 1996, vol. 100, pp. 3788-3798.

S. Maheshwari et al., "Layer Structure Preservation During Swelling, Pillaring, and Exfoliation of a Zeolite Precursor", Journal of American Chemical Soc., 2008, vol. 130, pp. 1507-1516.

J. Ruan et al., "Structure Elucidation of the Highly Active Titanosilicate Catalyst Ti-YNU-1", Angew. Chem. Int. Ed., 2005, vol. 44, pp. 6719-6723.

L. Slough et al., "Hydrodimerization of Benzene to Phenylcyclohexane over Supported Transition Metal Catalysts", Journal of Catalysis, 1969, vol. 13, pp. 385-396.

P. Wu et al., "Methodology for Synthesizing Crystalline Metallosilicates with Expanded Pore Windows Through Molecular Alkoxysilylation of Zeolitic Lamellar Precursors", Journal of American Chemical Soc., 2008, vol. 130, pp. 8178-8187.

L. Zhicheng et al., "Static Synthesis of High-Quality MCM-22 Zeolite with High $SiO_2/Al_2O_3$ Ratio", Chinese Science Bull, 2004, vol. 49, No. 6, pp. 556-561.

\* cited by examiner

ACTIVATION AND USE OF HYDROALKYLATION CATALYSTS

PRIORITY CLAIM TO RELATED APPLICATIONS

This application is a National Stage Application of International Application No. PCT/US2011/052241 filed Sep. 20, 2011, which claims priority to and the benefit of U.S. Provisional Application Ser. No. 61/391,845 filed Oct. 11, 2010, and European Application 10194026.0 filed Dec. 7, 2010, the disclosures of which are fully incorporated herein by their reference.

FIELD

The present invention relates to the activation of hydroalkylation catalysts and to the use of the activated catalysts in producing cycloalkylaromatic compounds, in particular cyclohexylbenzene.

BACKGROUND

The production of cycloalkylaromatic compounds, such as cyclohexylbenzene, is a commercially important reaction since the latter has potential as a source of phenol and cyclohexanone, which are important intermediates in the chemical industry with utility in, for example, the production of phenolic resins, bisphenol A, ε-caprolactam, adipic acid, and plasticizers.

Currently, the most common route for the production of phenol is the Hock process via cumene. This is a three-step process involving alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the demand for propylene is likely to increase. Thus, a process that does not require propylene as a feed and coproduces higher ketones, rather than acetone, may be an attractive alternative route to the production of phenol.

One such process involves the catalytic hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts.

An example of such a process is described in, for example, U.S. Pat. No. 6,037,513, in which an aromatic hydrocarbon, such as benzene, is contacted with hydrogen in the presence of a bifunctional catalyst, which has both hydrogenation activity and alkylation activity. In particular, the catalyst comprises a metal having hydrogenation activity, such as palladium, and a crystalline inorganic oxide material having alkylation activity and an X-ray diffraction pattern including d-spacing maxima at 12.4±0.25, 6.9±0.15, 3.57±0.07 and 3.42±0.07 Angstrom. The catalyst is produced by impregnating the crystalline inorganic oxide material with an aqueous solution of a palladium salt. The impregnated sample is then dried and calcined in air. Then prior to employing the catalyst in a hydroalkylation reaction, the catalyst is treated with 50 cc/min of flowing hydrogen for 2 hours at 300° C. and 1 atmosphere pressure. Although not stated in the '513 patent, this hydrogen treatment is employed to activate the catalyst by converting the palladium oxide produced in the calcination step to a more active form of palladium.

One problem of producing phenol via benzene hydroalkylation is the selectivity of the catalyst to cyclohexylbenzene since the process can produce significant quantities of unwanted by-products, particularly cyclohexane and heavies, such as dicyclohexylbenzene. Although many of these impurities can be removed by down-stream processing steps or further conversion processes such as transalkylation of dicyclohexylbenzene with benzene, such steps necessarily add cost to the overall process and hence there is significant interest in improving the cyclohexylbenzene selectivity of the hydroalkylation process.

According to the present invention, it has now been found that the cyclohexylbenzene selectivity of hydroalkylation catalysts, such as those disclosed in U.S. Pat. No. 6,037,513, can be improved by lowering the temperature of the hydrogen pre-treatment used to activate the catalyst. Lowering the pre-treatment temperature not only improves the catalyst selectivity but reduces the cost and time required to affect the pre-treatment process.

SUMMARY

The invention generally resides in a process for activating a hydroalkylation catalyst, the process comprising: (a) providing a hydroalkylation catalyst comprising a molecular sieve and a compound of a hydrogenation metal; and (b) activating the hydroalkylation catalyst in the presence of hydrogen to provide for a reduction of the compound of the hydrogenation metal; wherein the majority of the activation step (b) occurs at temperatures below about 250° C. based on activation time.

DETAILED DESCRIPTION

Figure 1:
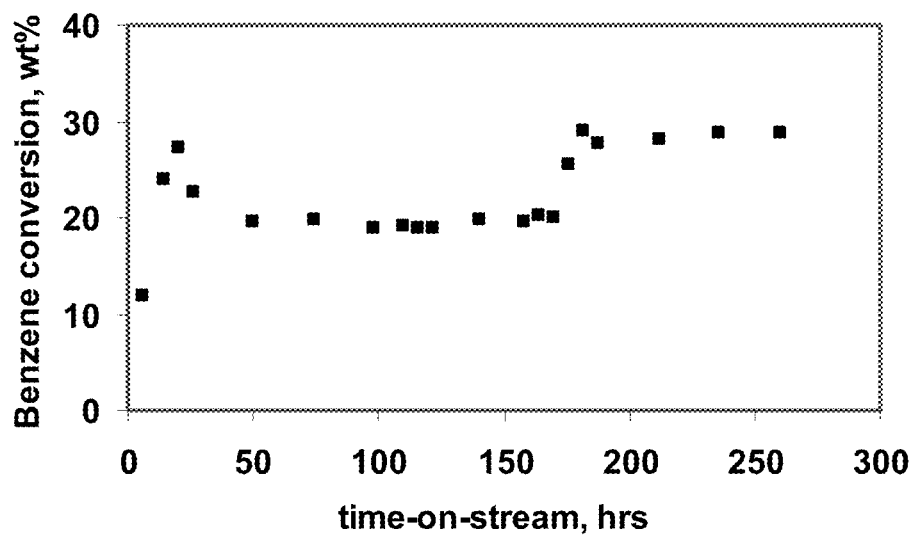
FIG. 1 is a graph of benzene conversion against time on stream for the hydroalkylation process of Example 1 and Example 2.

Described herein is a process for activating a hydroalkylation catalyst by treating the catalyst with hydrogen at a temperature of less than about 250° C. Also described is the use of the activated catalyst in the hydroalkylation of aromatic compounds to produce cycloalkylaromatic compounds. The present process is particularly intended for the hydroalkylation of benzene to produce cyclohexylbenzene for use as a precursor in the production of phenol and cyclohexanone. The remaining discussion will therefore focus on this particular embodiment, although it is to be appreciated that the present process is equally applicable to the production of other alkylaromatic compounds.

Production of the Cyclohexylbenzene

The hydroalkylation of benzene to produce cyclohexylbenzene proceeds according to the following reaction (1):

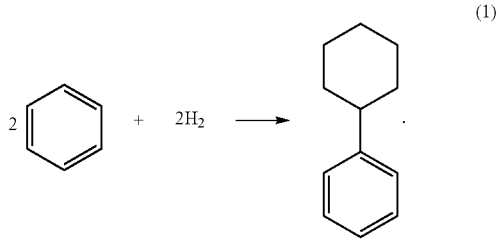 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

The hydroalkylation reaction is effected in the presence of a bifunctional catalyst comprising a molecular sieve and a hydrogenation metal. In one preferred embodiment, the molecular sieve comprises an MCM-22 family material. The term "MCM-22 family material" (or "material of the MCM-22 family" or "molecular sieve of the MCM-22 family"), as used herein, includes molecular sieves made from a building block unit cell, which unit cell has the MWW framework topology. A unit cell is a spatial arrangement of atoms which if tiled in three-dimensional space describes the crystal structure. MWW framework topology is disclosed and described in the "Atlas of Zeolite Framework Types", Fifth Edition, 2001, the entire content of which is incorporated as reference.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Irrespective of how the hydrogenation metal is deposited on the composite catalyst described above, the product of the deposition is normally an oxidized form of the metal rather than the elemental metal. Thus, prior to use in the hydroalkylation reaction, the catalyst must be activated by at least partial reduction of the metal compound into its zerovalent, elemental state. Conventional methods of reducing oxides of hydrogenation metals, such as palladium, involve gas phase treatment with hydrogen at relatively high temperature, normally at about 300° C. or higher. Unexpectedly, however, it has now been found that, by conducting the hydrogen treatment at lower temperatures, the selectivity of the catalysts to cyclohexylbenzene is increased and its selectivity to dicyclohexylbenzene is decreased. In addition, by using lower reduction temperatures, closer to or the same as those used in the subsequent hydroalkylation reaction, it is possible to effect the reduction in situ in the hydroalkylation reactor without the need to upgrade the temperature capacity of the reactor.

In one embodiment, the majority of the activation of the hydroalkylation catalyst is conducted at a temperature of less than about 250° C. based on activation time. In another embodiment, the majority of the activation of the hydroalkylation catalyst is conducted at a temperature of less than about 200° C. In another embodiment, the majority of the activation step (b) occurs at temperatures greater than 25° C. based on activation time. In other embodiments, at least 60%, at least 70%, at least 80%, at least 90%, and substantially all of the activation of the hydroalkylation catalyst is conducted at a temperature of less than about 250° C. In these embodiments, the activation temperature upper limit may be 240° C., 230° C., 220° C., 210° C., 200° C., 190° C., 180° C., 170° C., 160° C., 150° C., 140° C., 130° C., 120° C., 110° C., and 100° C.; and the lower limit temperature may be 0° C., 10° C., 20° C., 30° C., 40° C., 50° C., 60° C., 70° C., 80° C., and 90° C. with ranges from any lower limit to any upper limit being contemplated.

In particular, in the present process the activation of the hydroalkylation catalyst is conducted by heating the catalyst or a precursor thereof in a hydrogen-containing atmosphere at a temperature of about 25° C. to about 250° C., such as about 25° C. to about 200° C., for example about 50° C. to about 150° C., and a pressure of about 0 to 4000 kPa, gauge, such as about 0 to about 250 kPa, gauge. The time of the hydrogen treatment varies with the temperature employed but generally is at least 0.5 hour, such as from about 0.5 hour to about 100 hours, for example from about 1 hour to about 10 hours, such as for about 1 hour to about 5 hours. Generally, the hydrogen treatment is conducted in the hydroalkylation reactor.

In one embodiment, the catalyst activation is effected in the presence of a liquid phase diluent, such as a saturated hydrocarbon or unsaturated hydrocarbon, further such as a liquid aliphatic or aromatic hydrocarbon, particularly benzene. The liquid diluent improves the heat capacity of the hydroalkylation catalyst, thereby reducing the time required for the catalyst to reach the temperature required for the hydrogen reduction to proceed.

In some embodiments, prior to activation of the catalyst, it is necessary to reduce the water content of the hydroalkylation catalyst to obtain a catalyst that delivers a higher hydroalkylation conversion. In one embodiment, the catalyst is heated at a temperature below 200° C. for a sufficient period of time to reduce the water content to an acceptable level. In other embodiments, the temperature upper limit for the water reduction step may be 190° C., 180° C., 170° C., 160° C., 150° C., 140° C., 130° C., 120° C., 110° C., 100° C., 90° C., and 80° C.; and the lower limit temperature may be 0° C., 10° C., 20° C., 30° C., 40° C., 50° C., 60° C., and 70° C. with ranges from any lower limit to any upper limit being contemplated. The water reduction step may be facilitated by flowing any dry gas across the catalyst bed such as hydrogen or nitrogen. The water reduction step may occur for a sufficient period of time to reduce the water content such as for at least 0.1 hours, 0.5 hours, 1.0 hours, 1.5 hours, and 2.0 hours. An acceptable water content level of the hydroalkylation catalyst after water reduction step, but prior to activation step, may be a water content of no greater than 15 wt % such as from 1 wt % to 12 wt %.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa.

Although the hydroalkylation reaction using an MCM-22 family zeolite catalyst activated by the process described herein is highly selective towards cyclohexylbenzene, the effluent from the hydroalkylation reaction may contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically affected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

The cyclohexylbenzene product from the hydroalkylation reaction and any downstream transalkylation or dealkylation reaction is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 mol % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 wt % to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes smectite clay, such as an acidic montmorillonite silica-alumina clay, as described in U.S. Pat. No. 4,870,217, the entire disclosure of which is incorporated herein by reference.

The invention will now be more particularly described with reference to the following non-limiting Example and the accompanying drawings.

In the examples, a catalyst comprising 0.15 wt % Pd/80 wt % MCM-49/20 wt % alumina was used. A mixture of 80% MCM-49, 20% alumina, and deionized (DI) water was extruded to form a catalyst for testing. The catalyst was used in extrudate form. The extrudate was then calcined and then ammonium exchanged with 1 N ammonium nitrate solution, followed by the final air calcination at 538° C. to form H-form extrudate. The resulting extrudate was then treated with anionic PdCl2 in HCl solution (nominally known as H2PdCl4) using an aqueous based incipient wetness impregnation method wherein the H2PdCl2 was diluted in DI water. The treated catalyst was air dried at 121° C. and calcined in air at 538° C. for 2 hours to form the 0.15 wt % Pd/80 wt % MCM-49/20 wt % alumina catalyst.

For each experiment, 700 mg of the resultant catalyst was mixed with 1 gram of about 40 mesh quartz chips, and the mixture was packed into a ¼ inch (0.64 cm) internal diameter stainless steel reactor operating in down-flow mode.

EXAMPLE 1

Invention

The catalyst was treated by heating the reactor to 145° C. at 0 kPa, gauge under a flow of 47 microliter/min of benzene and 25 standard cubic centimeters per minute (sccm) of hydrogen wherein the reactor temperatures were ramped to 145° C. at 1° C./min.

The hydroalkylation reaction was run at 145° C. and 145 psig (1000 kPa, gauge) total reactor pressure at a weight hourly space velocity (WHSV) of 3.53 hr$^{-1}$. The effluent from the reactor was analyzed using an offline gas chromatograph equipped with a flame ionization detector. All the hydrocarbons were analyzed and the results were normalized.

EXAMPLE 2

Comparative

To compare the effect of high temperature activation on heavies selectivity, at around 190 hrs time-on-stream the benzene flow was stopped, and reactor was purged with 50 sccm of hydrogen at 50 psig (445 kPa, gauge). The reactor temperature was then ramped from 145° C. to 300° C., and held at 300° C. for 2 hours under a flow of 25 sccm of hydrogen. After the reduction, the reactor temperature was reduced to 145° C., and hydrogen and benzene feeds were restarted at 25 sccm and 47 microliter/min, respectively.

Figure 2:
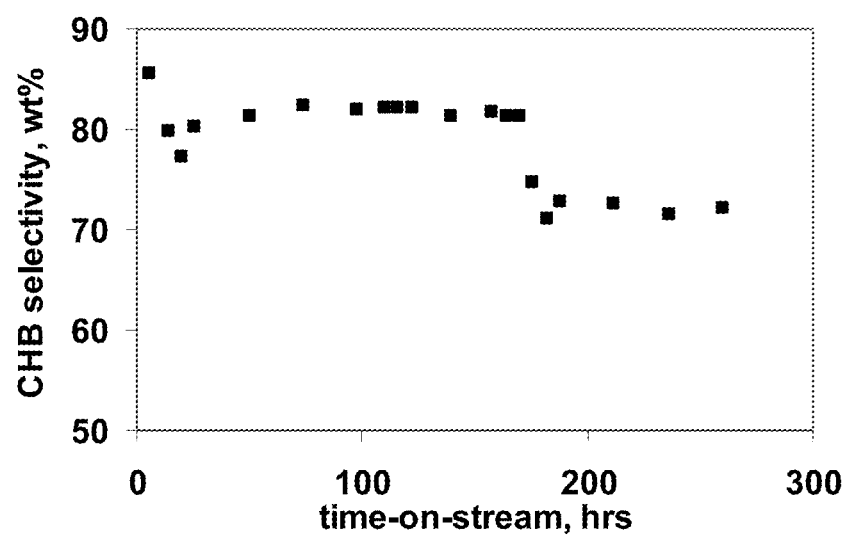
FIG. 2 is a graph of cyclohexylbenzene selectivity against time on stream for the hydroalkylation process of Example 1 and Example 2.
Figure 3:
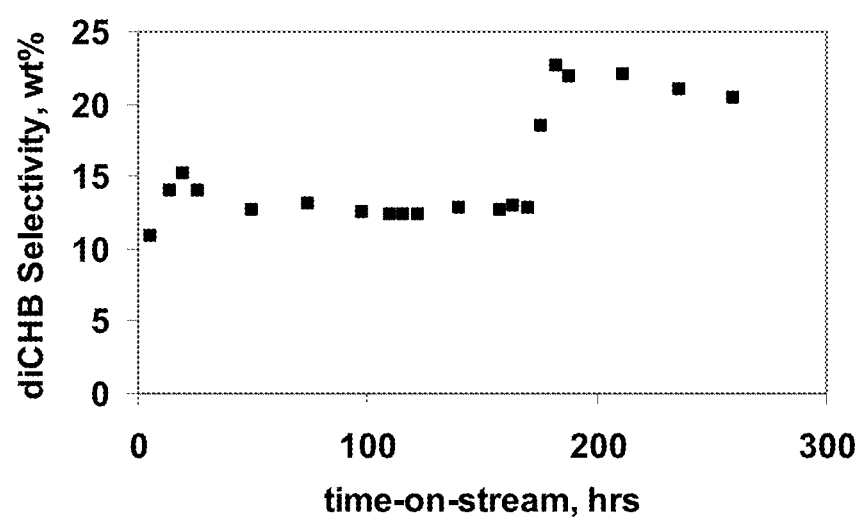
FIG. 3 is a graph of dicyclohexylbenzene selectivity against time on stream for the hydroalkylation process of Example 1 and Example 2.

The results from Example 1 and Example 2 are shown in the drawings, from which it will be seen that the high temperature activation increased the benzene conversion (FIG. 1) as compared with that achieved after the activation at 145° C. However, the cyclohexylbenzene selectivity decreased (FIG. 2) and the dicyclohexylbenzene selectivity increased (FIG. 3) after the high temperature activation.

EXAMPLE 3

Invention

The catalyst was treated by heating the reactor to 145° C. at 0 kPa, gauge under a flow of 80 microliter/min of benzene and 15 sccm of hydrogen wherein the reactor temperature was ramped to 145° C. at 1° C./min.

The hydroalkylation reaction was then run at 145° C. and 145 psig (1000 kPa, gauge) total reactor pressure at a weight hourly space velocity (WHSV) of 2.5 hr$^{-1}$. The effluent from the reactor was analyzed using an offline gas chromatograph equipped with a flame ionization detector. All the hydrocarbons were analyzed and the results were normalized.

The activation of Example 3 yielded a benzene conversion after two days of time-on-stream of approximately 12 wt % to 15 wt % while yielding a cyclohexylbenzene selectivity of approximately 80 wt % to 84 wt %.

EXAMPLE 4

Invention

The catalyst was treated under the same conditions as Example 3 with the exception that the catalyst bed was flooded with benzene prior to establishing benzene and hydrogen flow. The reactor temperature was ramped to 145° C. at 1° C./min.

The hydroalkylation reaction was run at 145° C. and 165 psig (1139 kPa, gauge) total reactor pressure at a weight hourly space velocity (WHSV) of 2.5 hr$^{-1}$. The effluent from the reactor was analyzed using an offline gas chromatograph equipped with a flame ionization detector. All the hydrocarbons were analyzed and the results were normalized.

The activation of Example 4 yielded a benzene conversion after two days of time-on-stream of approximately 12 wt % to 15 wt % while yielding a cyclohexylbenzene selectivity of approximately 80 wt % to 84 wt % which was the same results as in Example 3.

EXAMPLE 5

Invention

The catalyst was treated prior to hydroalkylation using the flowing steps. The catalyst was at least partially dehydrated by heating the reactor to 145° C. at 0 kPa, gauge. The catalyst used in Examples 2 to 4 was estimated to contain 15 wt % water. First, the catalyst was treated with 50 cubic centimeters per minute of nitrogen at 100° C. at 0 kPa, gauge for 2 hours. Second, the catalyst bed was then flooded with benzene. Third, benzene and hydrogen flow was established at 80 microliter/min of benzene and 15 sccm of hydrogen wherein the reactor temperature was ramped to 145° C. at 1° C./min. Experiment 5 was conducted twice to determine repeatability.

The hydroalkylation reaction was run at 145° C. and 145 psig (1000 kPa, gauge) total reactor pressure at a weight hourly space velocity (WHSV) of 2.5 hr$^{-1}$. The effluent from the reactor was analyzed using an offline gas chromatograph equipped with a flame ionization detector. All the hydrocarbons were analyzed and the results were normalized.

The activation of Example 5 yielded a benzene conversion after two days of time-on-stream of approximately 25 wt % and 30 wt % for each of the two tests while yielding a cyclohexylbenzene selectivity of approximately 80 wt % to 84 wt % for both tests.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process comprising:
   (a) providing a hydroalkylation catalyst comprising an MCM-22 family molecular sieve and a compound of a hydrogenation metal selected from palladium, ruthenium, nickel, zinc, tin, cobalt and mixtures thereof; and
   (b) activating the hydroalkylation catalyst in the presence of hydrogen and a liquid phase diluent comprising an aromatic compound to provide for a reduction of the compound of the hydrogenation metal;
   wherein the majority of the activation step (b), based on activation time, occurs at temperatures below 250° C.

2. The process of claim 1, wherein substantially the entire activation step (b), based on activation time, occurs at temperatures below 200° C.

3. The process of claim 1, wherein the majority of the activation step (b), based on activation time, occurs at temperatures greater than 25° C.

4. The process of claim 1, further comprising:
   (c) reducing the water content of the hydroalkylation catalyst prior to activating step (b).

5. The process of claim 1, wherein the activating step (b) is conducted in situ.

6. The process of claim 1, wherein the activating step (b) is conducted for at least 1 hour.

7. The process of claim 1, wherein the activating step (b) is conducted for at least 5 hours.

8. The process of claim 1, wherein the majority of the activation step (b), based on activation time, occurs at temperatures between 0° C. and 200° C.

9. The process of claim 1, wherein the majority of the activation step (b), based on activation time, occurs at temperatures between about 0° C. and about 150° C.

10. The process of claim 1, wherein the activating step (b) is conducted at a pressure of about 0 to about 4000 kPa, gauge.

11. The process of claim 1, wherein the diluent comprises benzene.

12. The process of claim 1, wherein the hydrogenation metal comprises palladium.

13. A process for activating a hydroalkylation catalyst, the process comprising:
   (a) providing a hydroalkylation catalyst comprising an MCM-22 family molecular sieve and a compound of a hydrogenation metal selected from palladium, ruthenium, nickel, zinc, tin cobalt, and mixtures thereof;
   (b) reducing the moisture of the hydroalkylation catalyst; and
   (c) activating the hydroalkylation catalyst in the presence of hydrogen and in the presence of a liquid phase diluent comprising an aromatic compound to provide for a reduction of the compound of the hydrogenation metal wherein the hydrogen at least partially dissolves in the liquid phase diluent;
   wherein the majority of the activation step (c), based on activation time, occurs at temperatures of below 250° C.

* * * * *